United States Patent
Wado et al.

(10) Patent No.: US 7,807,061 B2
(45) Date of Patent: Oct. 5, 2010

(54) OPTICAL GAS CONCENTRATION DETECTOR AND METHOD OF PRODUCING STRUCTURE USED IN THE DETECTOR

(75) Inventors: Hiroyuki Wado, Toyota (JP); Kazuhiko Kanoh, Toyoake (JP)

(73) Assignee: DENSO CORPORATION, Kariya (JP)

( * ) Notice: Subject to any disclaimer, the term of this patent is extended or adjusted under 35 U.S.C. 154(b) by 483 days.

(21) Appl. No.: 11/822,748

(22) Filed: Jul. 10, 2007

(65) Prior Publication Data

US 2008/0190175 A1   Aug. 14, 2008

(30) Foreign Application Priority Data

Jul. 19, 2006   (JP) .............. 2006-196659

(51) Int. Cl.
C23F 1/00   (2006.01)

(52) U.S. Cl. .............. 216/2; 216/24; 216/26; 216/74

(58) Field of Classification Search .......... 216/2, 216/24, 26, 74
See application file for complete search history.

(56) References Cited

U.S. PATENT DOCUMENTS

| 7,123,216 | B1* | 10/2006 | Miles | 345/54 |
| 7,307,716 | B2 | 12/2007 | Silver | |
| 7,477,377 | B2 | 1/2009 | Silver | |
| 2004/0211753 | A1* | 10/2004 | Shimizu et al. | 216/26 |
| 2005/0110104 | A1* | 5/2005 | Boettiger et al. | 257/432 |
| 2005/0133478 | A1 | 6/2005 | Kim et al. | |
| 2005/0134836 | A1 | 6/2005 | Paldus et al. | |

FOREIGN PATENT DOCUMENTS

| EP | 1 666 868 A1 | 6/2006 |
| JP | 05150103 A * | 6/1993 |
| JP | 2005-147962 A | 6/2005 |
| JP | 2003-185803 A | 7/2005 |
| WO | WO 97/49983 | 12/1997 |

OTHER PUBLICATIONS

Office Action dated Feb. 17, 2010 from the German Patent Office in the corresponding German Application No. 10 2007 033 717.7-54 (and English Translation).
Bourouina, T. et al. "The MEMSNAS Process: Microloading Effect for Micromachining 3-D Structures of Nearly All Shapes." Journal of Microelectromechanical Systems, vol. 13, No. 2, pp. 190-199, Apr. 2004.

* cited by examiner

Primary Examiner—Binh X Tran
(74) Attorney, Agent, or Firm—Posz Law Group, PLC

(57) ABSTRACT

A method of producing a structure by three-dimensionally processing a flat member includes a preparing, a first forming and a second forming. In the preparing, a substrate is prepared. In the first forming, an etching mask is formed on the substrate. The etching mask has at least two openings, and areas of the two openings are different from each other. In the second forming, at least a part of a three-dimension surface shape of the structure is formed on a surface of the substrate by a dry-etching on the substrate in accordance with the area of the opening of the etching mask.

9 Claims, 13 Drawing Sheets

OPTICAL GAS CONCENTRATION DETECTOR AND METHOD OF PRODUCING STRUCTURE USED IN THE DETECTOR

CROSS REFERENCE TO RELATED APPLICATION

This application is based on Japanese Patent Application No. 2006-196659 filed on Jul. 19, 2006, the disclosure of which is incorporated herein by reference in its entirety.

BACKGROUND OF THE INVENTION

1. Field of the Invention

The present invention relates to an optical gas concentration detector and a method of producing a structure used in the detector.

2. Description of Related Art

A gas molecule has a property of absorbing light having a predetermined wavelength, and this property is used in a variety of gas concentration detectors. Intensity of light absorbed by the gas molecule depends on an optical path length of light to be measured, and a gas concentration to be detected. Therefore, when the gas concentration is extremely low, the detector needs a long optical path length. Thus, a size of the gas concentration detector may become large.

JP-A-2005-147962 discloses a gas concentration detector. Light having the predetermined wavelength enters a gas cell of the gas concentration detector, in which a predetermined gas exists. A plane mirror disposed in the gas cell performs multiple reflections of the light, and the reflected light is received to detect the gas concentration. Thus, the optical path length can be increased by the multiple reflections. Therefore, the gas cell having a relatively small size can secure relatively long optical path length. Further, gas having relatively low concentration can sufficiently absorb light.

The above-described gas concentration detector needs a pair of mirrors, especially concave mirrors, capable of enclosing light in the gas cell. The concave mirror is made of a material, e.g., Si, Ge or ZnSe, making light to pass through, and the light has a wavelength range from mid-infrared to far-infrared in order to detect the gas concentration. However, when the concave mirror is made of this material, a surface of the concave mirror has to be grinded after machine processing. In this case, cost for producing the concave mirror may be increased. Therefore, the machine processing is required to be performed easily with high accuracy.

In contrast, US 2005/0133478 A1 (corresponding to JP-A-2005-181961) discloses a method of producing a concave mirror by using a silicon substrate (first layer). Specifically, a second layer is formed on the first layer. Etching rate is different between the first layer and the second layer. Then, a mask pattern is formed on the second layer. Thereafter, each layer is etched with each etching rate. Thus, lens can be formed on the silicon substrate.

However, laser diode (LD) or light-emitting diode (LED) having a high directivity is needed in JP-A-2005-147962, in order to perform the multiple reflections of light. In this case, quantum cascade laser light source may be used as a light source, because the quantum cascade laser light source can emit light having wavelength equal to or larger than 2 μm in the range from the mid-infrared to the far-infrared. When the quantum cascade laser light source is used, gas can have a high coefficient of absorbing light, so that the gas can be detected with a high sensitivity. However, the quantum cascade laser light source is expensive, so that it may not be practical to use the quantum cascade laser light source.

Therefore, an electric bulb using hot wire (heat ray) is generally used as the light source. The electric bulb can emit light having continuous wavelength, which depends on a temperature of the light source. However, the directivity of the electric bulb is low compared with that of the LD or LED. That is, a light beam in the gas cell disclosed in JP-A-2005-147962 is not stable, so that the optical path length cannot be secured to be stable.

Further, the difference in the etching rate between the first and second layers is used to produce the concave mirror in JP-A-2005-181961. However, unevenness (variation) may be generated in a shape of the concave mirror due to unevenness (variation) in a thickness of the second layer.

In addition, JP-A-2003-185803 discloses a method of forming a concave surface in a trench formed in a substrate by using isotropic etching. This method may be superior to the method disclosed in JP-A-2005-181961 in a point of controlling the shape of the concave mirror. However, in order to perform the multiple reflections, mirror has to have a size in a millimeter order, for example. The method disclosed in JP-A-2003-185803 can form a mirror having a size in a micrometer order, but cannot form a mirror having a size in the millimeter order.

SUMMARY OF THE INVENTION

In view of the foregoing and other problems, it is a first object of the present invention to provide an optical gas concentration detector, in which an optical path length is secured to be long even when en electric bulb is used as a light source. It is a second object of the present invention to provide a method of producing a structure as a mirror used in the optical gas concentration detector.

According to a first example of the present invention, a method of producing a structure by three-dimensionally processing a flat member includes a preparing, a first forming and a second forming. In the preparing, a substrate is prepared. In the first forming, an etching mask is formed on the substrate. The etching mask has at least two openings, and areas of the two openings are different from each other. In the second forming, at least a part of a three-dimension surface shape of the structure is formed on a surface of the substrate by a dry-etching on the substrate in accordance with the area of the opening of the etching mask.

According to a second example of the present invention, an optical gas concentration detector for measuring a gas concentration includes a first mirror, a second mirror, a light source and a detector. The first mirror has a first concave surface as a reflection face. The second mirror paired with the first mirror has a second concave surface as a reflection face. The light source emits light. The detector detects an intensity of light having a predetermined wavelength. The first concave surface and the second concave surface are located to oppose to each other to form a space, into which air including gas to be measured is introduced. The first mirror and the second mirror perform multiple reflections of the emitted light between the first concave surface and the second concave surface.

Accordingly, the optical path length in the optical gas concentration detector can be secured to be long.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF PREFERRED EMBODIMENTS

First Embodiment

Figure 1:
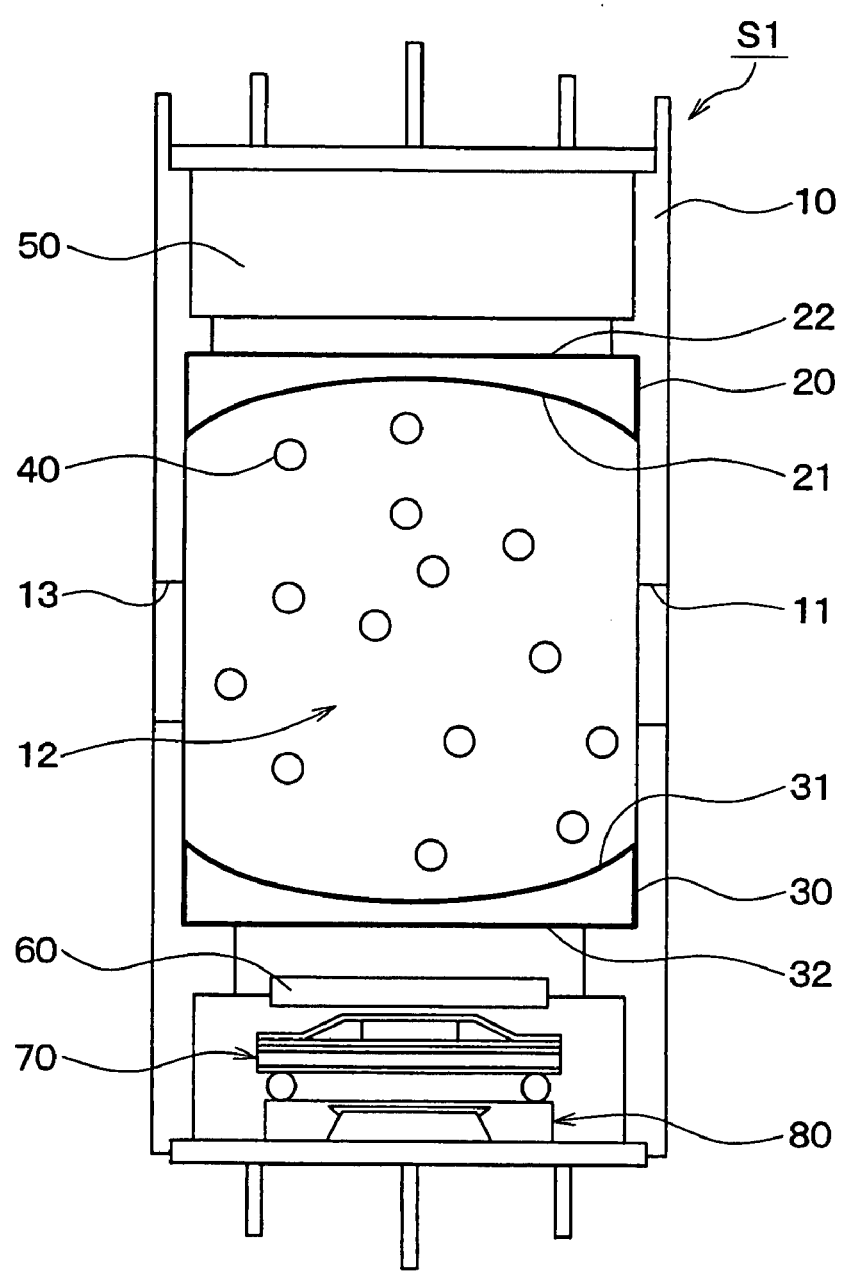
FIG. 1 is a schematic diagram showing a gas concentration detector according to a first embodiment of the present invention.

A gas concentration detector S1 shown in FIG. 1 detects a concentration of gas, e.g., $CO_2$ or HC, in air. The gas absorbs light having wavelength in mid-infrared range, for example. The gas concentration detector S1 measures gas concentration by detecting an intensity of the light having the wavelength in the mid-infrared range.

As shown in FIG. 1, the gas concentration detector S1 includes a tube-shaped case 10, in which a first mirror 20 and a second mirror 30 paired with the first mirror 20 are fixed.

Each of the first mirror 20 and the second mirror 30 has a plane-concave structure. The first mirror 20 has a concave surface 21, and the second mirror 30 has a concave surface 31. The concave surface 21 and the concave surface 31 oppose to each other. A focus of the first mirror 20 is positioned at an approximately center of the concave surface 31 of the second mirror 30. A focus of the second mirror 30 is positioned at an approximately center of the concave surface 21 of the first mirror 20. That is, an interval between the first mirror 20 and the second mirror 30 corresponds to a focus distance between the concave surfaces 21, 31.

The mirror 20, 30 is made of a material, e.g., Si or Ge, having a high transmittance relative to infrared light. The concave surface 21, 31 of the mirror 20, 30 has a reflection film thereon, and has a high reflectance equal to or larger than 90%. In the first embodiment, the concave surface 21, 31 has the reflectance of 95%. Light introduced between the pair of the mirrors 20, 30 can have an optical path length, which is ten times as long as the interval between the mirrors 20, 30.

The mirror 20 has a flat face 22 opposite to the concave surface 21, and the mirror 30 has a flat face 32 opposite to the concave surface 31. The flat face 22, 32 has an antireflection film thereon, and has a relatively low reflectance. The concave surface 21, 31 has a diameter of 3 mm, for example.

The case 10 has an air hole 11, 13 between the mirrors 20, 30. Gas 40 enters the case 10 through the air hole 11, 13. Thereby, the gas 40 is enclosed in a space 12 formed by an inner wall of the case 10 and the concave surfaces 21, 31 of the mirrors 20, 30.

A light source 50 is fixed to a first end of the case 10. The first end of the case 10 opposes to the flat face 22 of the first mirror 20. The light source 50 includes a light-emitting source (not shown). The light-emitting source is an infrared light source, and has a high-temperature, e.g., about 1000° C., filament. Thus, the light source 50 can emit light having wavelength in the infrared range.

Light emitted from the light source 50 passes through the first mirror 20, and is introduced into the space 12 of the case 10. The mirrors 20, 30 performs multiple reflections of the introduced light between the concave surfaces 21, 31.

Further, a band pass filter 60 is fixed to a second end of the case 10. The second end of the case 10 opposes to the flat face 32 of the second mirror 30. The band pass filter 60 eliminates light having wavelength in a range from visible to near-infrared, and far-infrared.

A spectroscopic device 70 is disposed adjacent to the band pass filter 60, opposite to the second mirror 30. The spectroscopic device 70 is constructed with a Fabry-Perot type device, for example, and includes a spectroscopic element.

The spectroscopic element disperses light passing through the band pass filter 60, and emits light having a predetermined wavelength.

However, according to a principle of the spectroscopic device 70, the spectroscopic device 70 can disperse only light having wavelength of some micrometer. Therefore, the band pass filter 60 is used for eliminating light having wavelength in the range from visible to near-infrared and far-infrared, i.e., except for mid-infrared.

The spectroscopic device 70 is a known optical device, so that detailed description of the spectroscopic device 70 is omitted here. The spectroscopic device 70 is described in details in the textbook entitled HIKARI MAIKURO-MASHIN by Sawada Renshi, Hane Kazuhiro and Higurashi Eiji at pages 30-33 and 205-210 published by Ohmsha, Ltd.

An infrared sensor device 80 is disposed adjacent to the spectroscopic device 70, opposite to the band pass filter 60. The infrared sensor device 80 includes a light-receiving element to receive the light having the predetermined wavelength emitted from the spectroscopic device 70. Then, the infrared sensor device 80 outputs a voltage signal outside, and the voltage signal corresponds to an intensity of the received light.

The band pass filter 60, the spectroscopic device 70 and the infrared sensor device 80 construct one package. The package is disposed at the second end of the case 10, opposite to the first end of the case 10 at which the light source 50 is disposed.

The light source 50, the first mirror 20, the second mirror 30, the band pass filter 60, the spectroscopic device 70 and the infrared sensor device 80 are located along a longitudinal axis of the case 10, i.e., in alignment with each other. Thereby, light emitted from the light source 50 passes through the first mirror 20, and is enclosed between the first and second mirrors 20, 30. The first and second mirrors 20, 30 perform the multiple reflections of the enclosed light, and the multiply reflected light passes through the second mirror 30. Then, the light enters the infrared sensor device 80 through the band pass filter 60 and the spectroscopic device 70.

Next, a method of producing the mirror 20, 30 used in the gas concentration detector S1 will be described with reference to FIGS. 2, 3A and 3B. In the first embodiment, the mirror 20, 30 is produced by processing a substrate made of Si or Ge to have a predetermined shape.

Figure 3A:
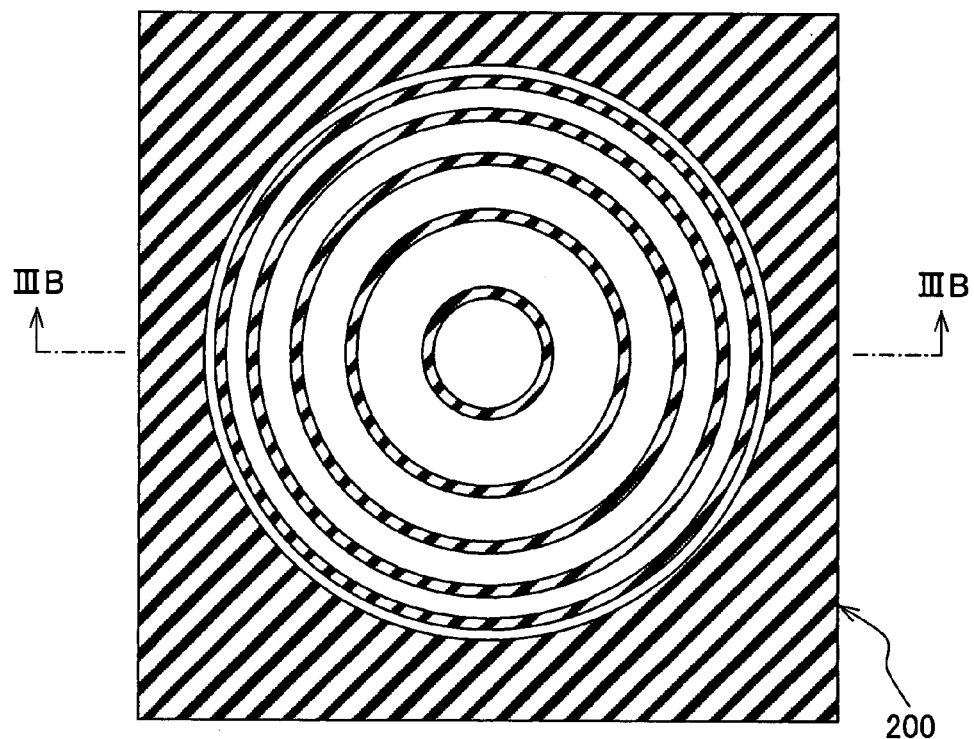
FIG. 3A is a plan view showing a mask on a silicon substrate.
Figure 3B:
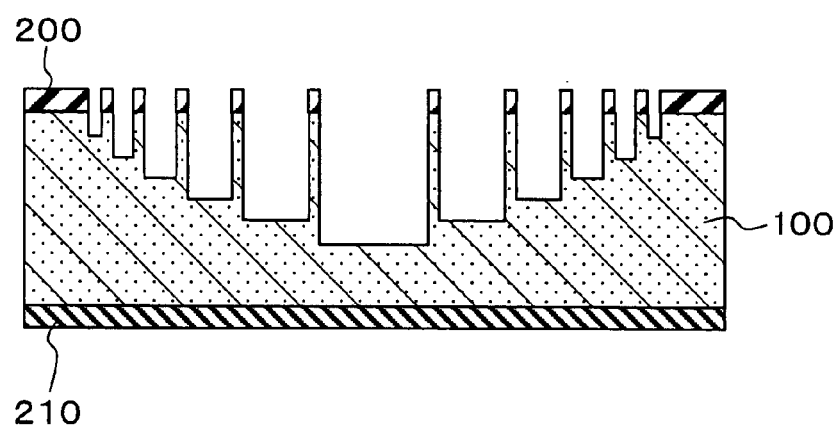
FIG. 3B is a schematic cross-sectional view showing the mask and the silicon substrate taken along line IIIB-IIIB in FIG. 3A.

Specifically, the processing is performed by using a microloading effect, in which etching of the substrate is shallow at a mask having a relatively narrow opening width, and etching of the substrate is deep at a mask having a relatively wide opening width, as shown in FIG. 3B.

Figure 2:
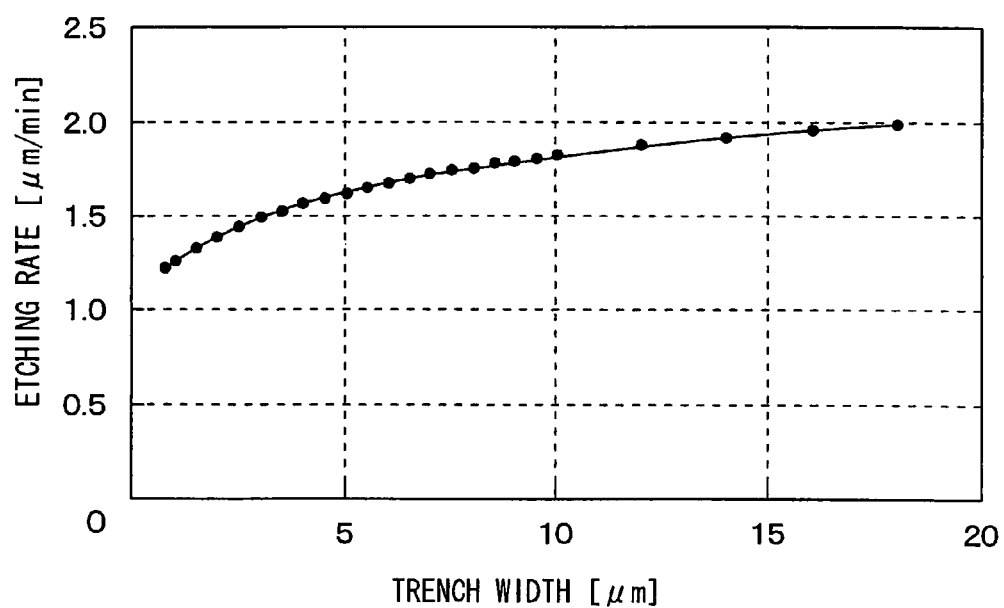
FIG. 2 is a graph showing a relationship between a trench width and an etching rate.

FIG. 2 shows a relationship between a trench width, i.e., opening width of the mask, in the substrate and an etching rate of the substrate, which is measured when the trench width is changed in a range of 0.8-18 µm. As shown in FIG. 2, as the trench width is increased, the etching rate is increased, so that the etching becomes deep.

In the first embodiment, as shown in FIGS. 3A and 3B, a silicon (Si) substrate 100 is prepared, and etched with a mask 200 by using the microloading effect, in order to form the concave surface 21, 31 of the mirror 20, 30.

The mask 200 has a shape of concentric circles on the silicon substrate 100. A hatching part of FIG. 3A is the mask 200 left on the silicon substrate 100 in FIG. 3B, and a blank part of FIG. 3A is an open area, under which the silicon substrate 100 is etched, as shown in FIG. 3B.

An interval between adjacent concentric circles of the mask 200 becomes smaller toward a peripheral part of the mask 200. Thereby, as shown in FIG. 3B, the etching becomes deeper toward a center part of the substrate 100, and the etching becomes shallower toward a peripheral part of the substrate 100. Thus, the depth of the etching relative to the silicon substrate 100 can be controlled in accordance with the width of the opening of the mask 200, in order to form the concave surface 21, 31 of the mirror 20, 30. In addition, another mask 210 is formed on a whole back face of the silicon substrate 100, in order to prevent the back face of the silicon substrate 100 from being etched.

According to the etching method using the microloading effect, etching can be performed at a predetermined position of the silicon substrate 100 in a predetermined depth by only controlling the width of the opening of the mask 200. Therefore, the etching method can form a macroscopic outer shape of a convex surface other than the concave surface 21, 31. Further, if three-dimensional shape is needed, a curve surface can be freely formed. Next, a method of producing the mirror 20, 30 using the microloading effect will be described with reference to FIGS. 4A, 4B, 4C, 4D, 4E and 4F.

The mirror 20, 30 is made of a material capable of making light having wavelength in a range from mid-infrared to far-infrared to pass through. The material is Si, Ge or ZnSe, for example. A silicon substrate 110 is used as the material in the first embodiment.

Figure 4A:
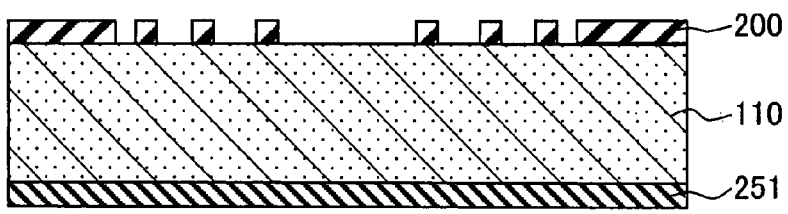
FIG. 4A is a schematic cross-sectional view showing a process of forming the mask.

As shown in FIG. 4A, the mask 200 is formed on the silicon substrate 110. Specifically, the silicon substrate 110 is prepared, and a front face and a back face of the silicon substrate 110 are thermally oxidized at about 1150° C. for approximately two hours. Thus, an oxidized film having a thickness, e.g., about 1 µm, is formed on both of the front face and the back face of the silicon substrate 110.

Thereafter, the mask 200 is formed by patterning the oxidized film formed on the front face of the silicon substrate 110. At this time, the opening width in the center part of the mask 200 is larger than that in the peripheral part of the mask 200. That is, as shown in 4A, the interval between the concentric circles of the mask 200 becomes narrower toward the peripheral part of the mask 200. At this time, the remained oxide film separates the openings, and has a small width of 1 µm to be completely oxidized in an oxidizing process shown in FIG. 4C. In addition, the oxidized film formed on the back face of the silicon substrate 110 is used as another mask 251.

Figure 4B:
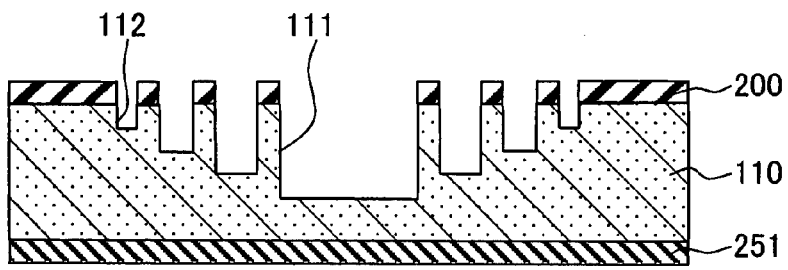
FIG. 4B is a schematic cross-sectional view showing a process of etching.

As shown in FIG. 4B, a dry etching is performed on the silicon substrate 110. Because the depth of the etching depends on the width of the opening of the mask 200, the center part of the substrate 110 is deeply etched to be a center deepest part of the concave surface 21, 31. Specifically, a concave part 111 is defined to be the deepest among the etched parts. In contrast, a concave part 112 to be the peripheral part of the concave surface 21, 31 is shallower than the concave part 111, because the interval between the openings of the mask 200 is narrow in the peripheral part.

Figure 4C:
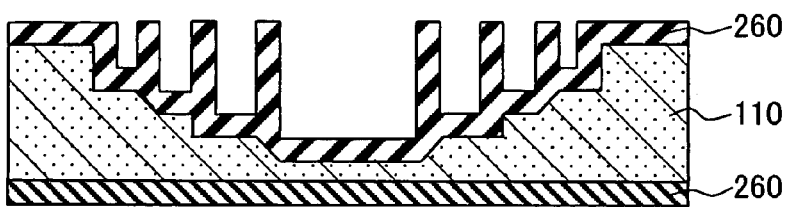
FIG. 4C is a schematic cross-sectional view showing a process of oxidizing.

As shown in FIG. 4C, the silicon substrate 110 exposed to outside is thermally oxidized. That is, the silicon substrate 110 not etched in the process shown in FIG. 4B is thermally oxidized similarly to the process shown in FIG. 4A. Thereby, the exposed silicon substrate can be oxidized to form an oxidized film 260 on the whole surface of the silicon substrate 110.

Figure 4D:
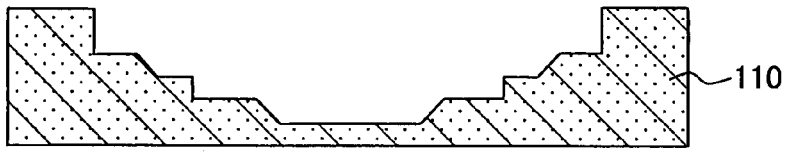
FIG. 4D is a schematic cross-sectional view showing a process of removing.

As shown in FIG. 4D, the silicon substrate 110 not etched in the process shown in FIG. 4B is removed. For example, fluorinated acid is used for removing the oxidized film 260. Thereby, a macroscopic concave shape can be formed on the front surface of the silicon substrate 110. The macroscopic concave shape still has projections and depressions in accordance with the interval between the openings of the mask 200.

Figure 4E:
FIG. 4E is a schematic cross-sectional view showing a process of a thermal treatment and FIG. 4F is a schematic cross-sectional view showing a process of forming a reflection film and an antireflection film.

As shown in FIG. 4E, a thermal treatment, e.g., about 1100° C., is performed on the silicon substrate 110 in a hydrogen atmosphere, for example. Thereby, the concave shape on the front surface of the silicon substrate 110 is liquidized, so that the projections and recessions disappear. Thus, the front surface of the silicon substrate 110 can function as a mirror.

Figure 4F:
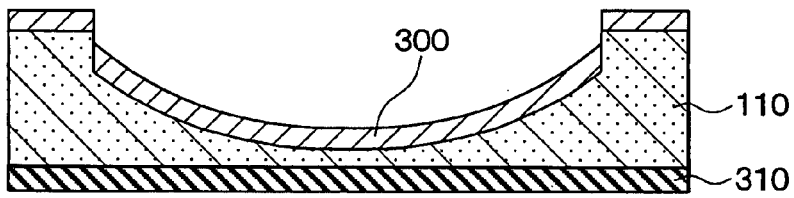

As shown in FIG. 4F, a reflection film 300 is formed on the front surface of the silicon substrate 110, and an antireflection film 310 is formed on the back face of the silicon substrate 110. Specifically, gold (Au) is evaporated and deposited on the front surface (concave shape) of the silicon substrate 110 to form the reflection film 300. The reflection film 300 has a thickness of about 0.2 µm and a reflection characteristic in a relatively wide band range. Next, SiN film having a thickness of about 0.5 µm is formed on the back face of the silicon substrate 110 as the antireflection film 310. Thus, the mirror 20, 30 used in the gas concentration detector S1 can be produced. The mirror 20, 30 is used as a part of the gas concentration detector S1.

The gas concentration detector S1 detects a gas concentration as described below. Air is introduced into the gas concentration detector S1 through the air hole 11, 13, and the light source 50 emits light. The light emitted from the light source 50 passes through the first mirror 20, and is introduced into the space 12 of the case 10. The mirrors 20, 30 perform the multiple reflections of the introduced light between the concave surfaces 21, 31. Thereby, light can have a long optical path length.

Air introduced into the space 12 includes $CO_2$ molecule, for example, and the molecule absorbs light having the predetermined wavelength, during the multiple reflections. Therefore, the light having the predetermined wavelength attenuates, and an intensity of the light having the predetermined wavelength is lowered. Thereafter, the light passes through the second mirror 30, and the band pass filter 60 removes light having wavelength in the range from visible to near-infrared and far-infrared. Then, the spectroscopic device 70 disperses light, and the dispersed light enters the infrared sensor device 80.

The infrared sensor device 80 outputs a voltage signal outside, and the voltage signal corresponds to an intensity of the light incident into the infrared sensor device 80 through the spectroscopic device 70. Thus, a gas concentration corresponding to the voltage signal can be provided.

According to the first embodiment, the concave surface 21, 31 is formed on the silicon substrate 110 by using the microloading effect, and the mirror 20, 30 having the concave surface 21, 31 is used in the gas concentration detector S1.

Due to the microloading effect, trenches having different depths can be formed in the silicon substrate 110, when the mask 200 has plural opening areas different from each other, because the etching becomes deeper as the opening area becomes larger. That is, a predetermined three-dimensional structure can be easily formed in the silicon substrate 110 by controlling area and position of the openings of the mask 200.

Further, when the microloading effect is used for processing the substrate 110, a processing degree of the silicon substrate 110 can be controlled by only the area of the opening of the mask 200. Therefore, a thickness of the mask 200 and an etching rate are not required to be adjusted. Thus, processing accuracy can be kept better. Further, unevenness (variation) of the processing can be reduced, and unevenness (variation) in the shape of the silicon substrate 110 can be reduced.

Further, a structure having a millimeter order size can be easily produced, which cannot be formed with a conventional art. This is because the trenches having different depths can be formed in the silicon substrate 110 due to the plural openings provided in the mask 200.

The gas concentration detector S1 can be constructed with the first and second mirrors 20, 30 formed as described above. That is, the concave surfaces 21, 31 of the mirrors 20, 30 are positioned to face each other, and the multiple reflections of light are performed between the mirrors 20, 30. Thus, the optical path length of light can be secured to be long.

Because the optical path length of light can be secured to be long, the gas 40 to be measured can sufficiently absorb light having the predetermined wavelength, even if the concentration of the gas 40 is relatively low. That is, a laser diode (LD) or light-emitting diode (LED) is not needed as the light-emitting source. When the light source 50 is used, the optical path length of light can be secured to be stable, so that gas having the relatively low concentration can be detected.

The concave surface 21, 31 can collect light and introduce the collected light to the opposing concave surface. Thereby, intensity of light reflected between the concave surfaces 21, 31 can be kept higher, so that the light can be easily and accurately detected. That is, when an electric bulb, for example, is used as the light source 50 in place of the LD or LED, the optical path length can be secured to be stable.

Second Embodiment

If the first mirror 20 has a relatively high reflectance, an amount of light incident into the first mirror 20 from the light source 50 may be reduced. In this case, a light source capable of emitting a large amount of light may be needed. Further, if the light source 50 is driven for a long time, the case 10 may be heated.

In contrast, in a second embodiment, a micro (membrane) heater 23 is embedded in a first mirror 20 as the light source capable of emitting the large amount of light. At this time, the light source 50 of the first embodiment is eliminated in the second embodiment. The other parts in the second embodiment may be made similar to the first embodiment. A gas concentration detector S2 of the second embodiment will be described below.

Figure 5:
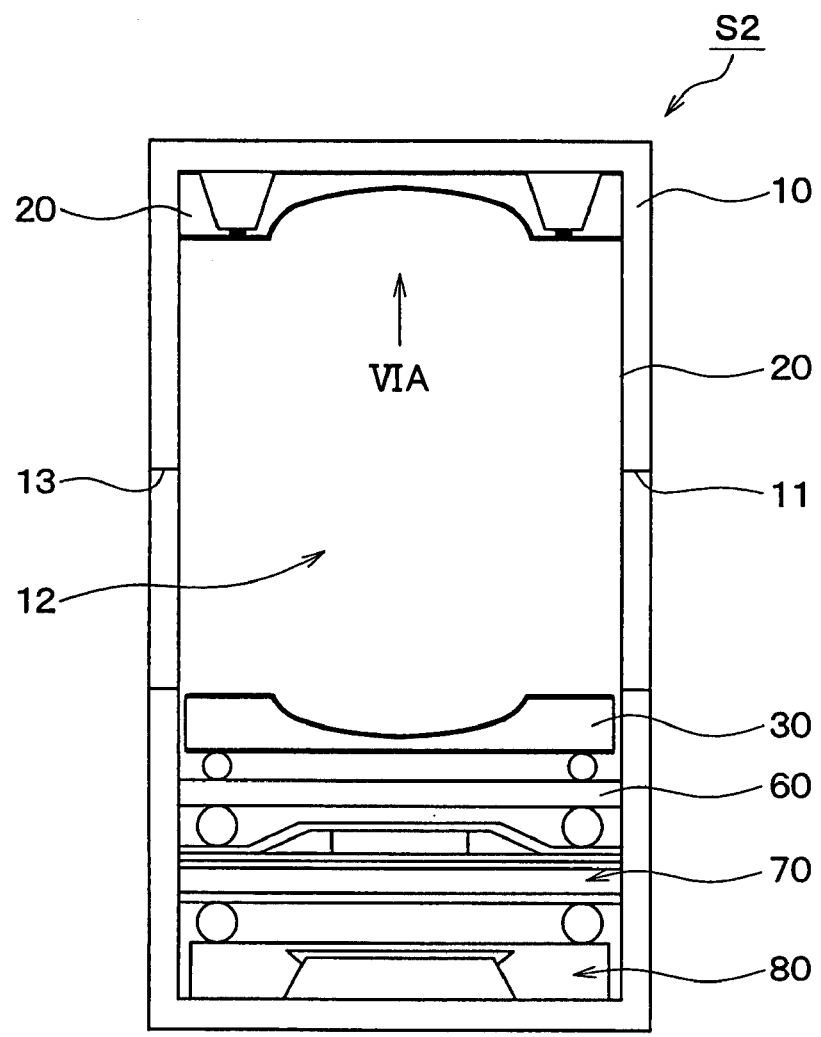
FIG. 5 is a schematic diagram showing a gas concentration detector according to a second embodiment of the present invention.
Figure 6A:
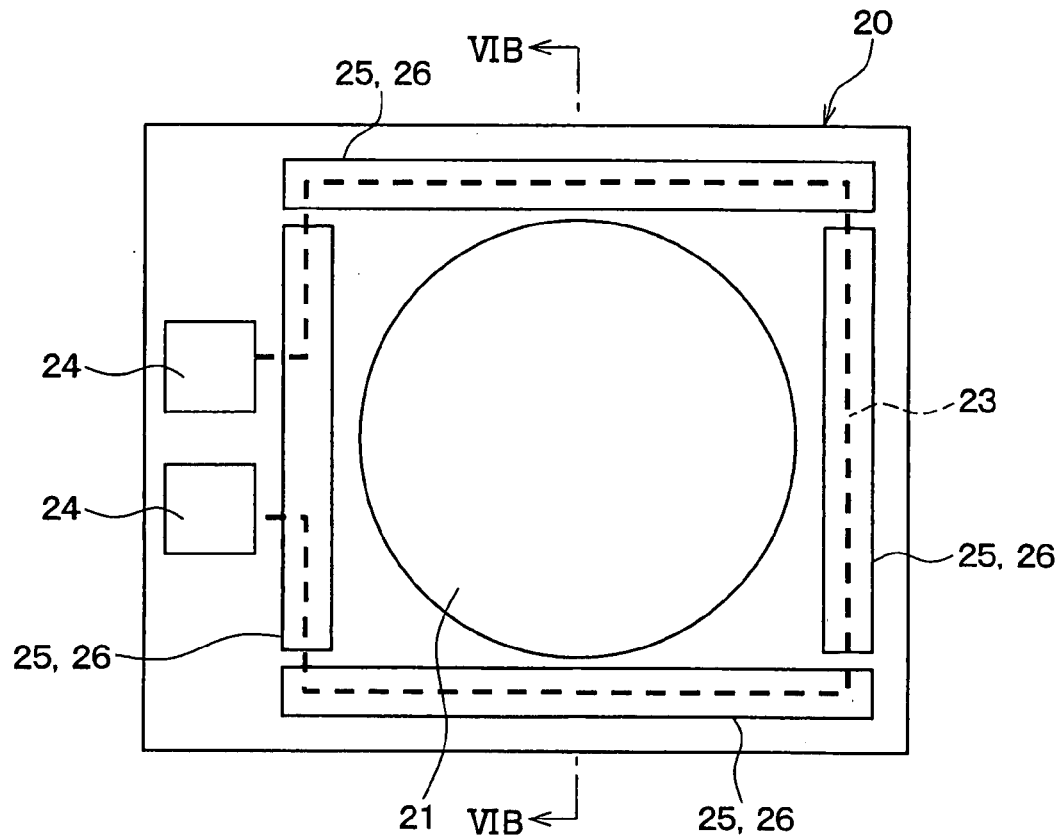
FIG. 6A is a schematic plan view showing a first mirror in an arrow VIA direction in FIG. 5.
Figure 6B:
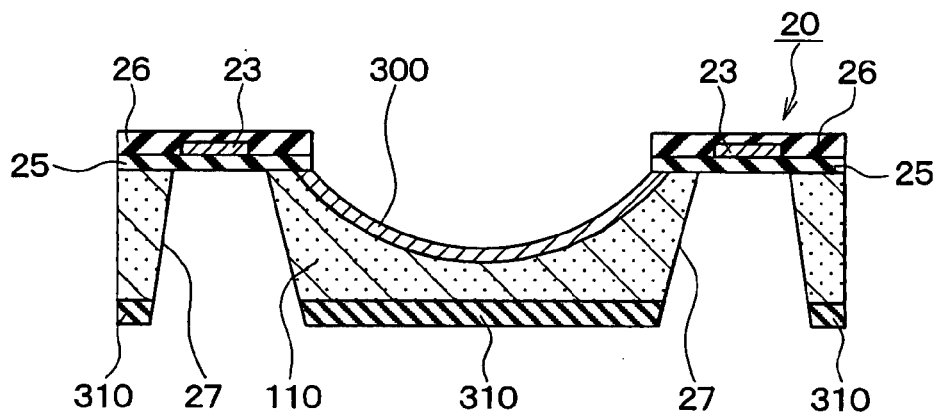
FIG. 6B is a schematic cross-sectional view taken along line VIB-VIB in FIG. 6A.

As shown in FIG. 5, the gas concentration detector S2 includes the first mirror 20, in which the micro heater 23 is embedded. As shown in FIGS. 6A and 6B, the micro heater 23 is disposed in a peripheral part of a front surface of the first mirror 20. The concave surface 21 is formed at the same front surface side. The front surface of the first mirror 20 corresponds to a lower surface of the first mirror 20 in FIG. 5. An electrode 24 is formed at each end of the micro heater 23. The micro heater 23 emits light when electricity is supplied between the electrodes 24.

Further, as shown in FIG. 6B, a membrane bottom film 25 is formed on the peripheral part of the front surface of the silicon substrate 110 as an insulation film. The micro heater 23 is formed on the membrane bottom film 25. A membrane top film 26 is formed to cover the micro heater 23 as an insulation film. A membrane is defined by the membrane bottom film 25 and the membrane top film 26. Further, the silicon substrate 110 corresponding to a position of the micro heater 23 is removed to form a concave part 27.

Thus, when the micro heater 23 is embedded in the first mirror 20 as the light source, an efficiency of light incident from the micro heater 23 into the space 12 can be increased.

Next, a method of producing the first mirror 20 of the second embodiment will be described with reference to FIGS. 7A, 7B, 7C and 7D. The second embodiment has the same processes shown in FIGS. 4A, 4B, 4C, 4D and 4E of the first embodiment. In order to form the membrane, a substrate made of Si(100) is used as the silicon substrate 110.

Figure 7A:
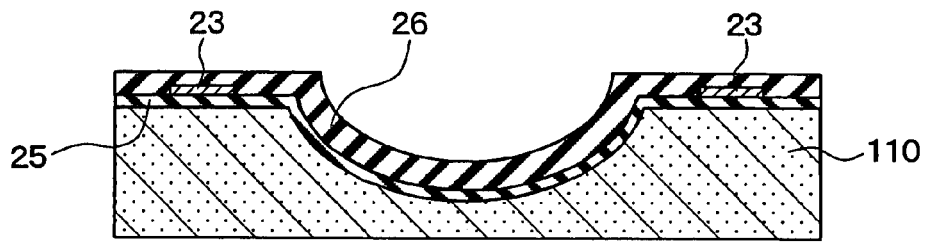
FIG. 7A is a schematic cross-sectional view showing a process of forming a membrane.

As shown in FIG. 7A, the membrane is formed on the silicon substrate 110. First, the membrane bottom film 25 is formed on the silicon substrate 110. Specifically, an insulation film combining a SiN film and a $SiO_2$ film is formed on the whole front surface of the silicon substrate 110 as the membrane bottom film 25 by using a low-pressure chemical vapor deposition (LPCVD) method. The insulation film may be any suitable kind of insulation film without departing from the scope of the present disclosure, and the method of forming the insulation film may be any suitable method without departing from the scope of the present disclosure.

Thereafter, platinum (Pt) film is formed on the membrane bottom film 25, and etching is performed to pattern the micro heater 23 shown in FIG. 6A. Further, another insulation film combining the SiN film and the $SiO_2$ film is formed as the membrane top film 26 to cover the micro heater 23 and the membrane bottom film 25.

Figure 7B:
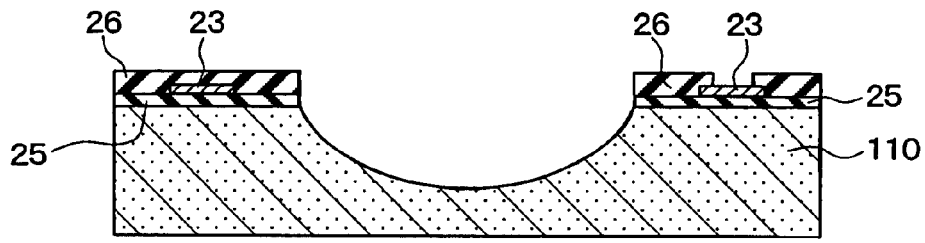
FIG. 7B is a schematic cross-sectional view showing a process of etching.

As shown in FIG. 7B, a part of the membrane top film 26 is removed by etching in order to arrange the electrode 24 for supplying electricity to the micro heater 23, and the membrane bottom film 25 and the membrane top film 26 formed on the concave surface 21 are removed by etching.

Figure 7C:
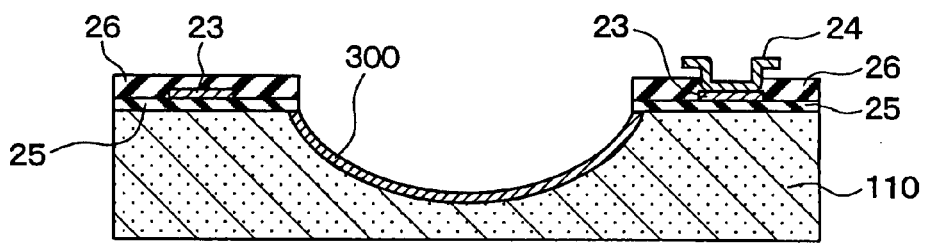
FIG. 7C is a schematic cross-sectional view showing a process of forming a reflection film and an electrode and FIG. 7D is a schematic cross-sectional view showing a process of forming an antireflection film and etching.

As shown in FIG. 7C, gold (Au) is evaporated and deposited on the front surface (concave surface 21) of the silicon substrate 110 to form the reflection film 300. The reflection film 300 has a thickness of about 0.2 µm and a reflection characteristic in a wide band range. Further, the electrode 24 is arranged at the etched part of the membrane top film 26.

Figure 7D:
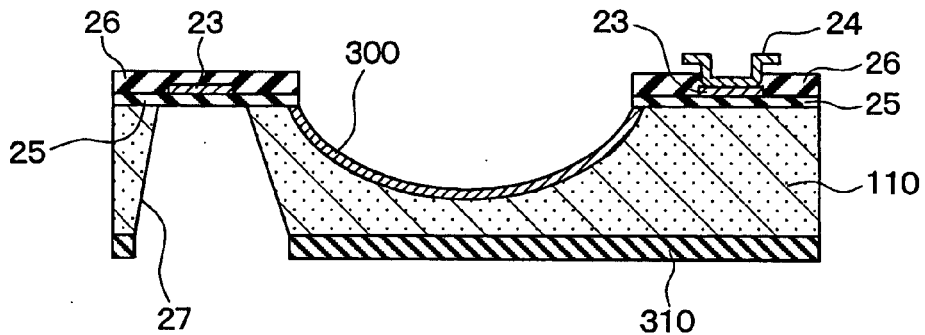

As shown in FIG. 7D, a SiN film having a thickness of about 0.5 µm is formed on a back face of the silicon substrate 110 as the antireflection film 310. Further, the antireflection film 310 opposing to the micro heater 23 is removed by patterning. Then, the silicon substrate 110 is soaked in an etching liquid from the back face. Therefore, the concave part 27 can be formed, because anisotropic etching is performed at the back face of the silicon substrate 110 from the removed part of the antireflection film 310. Thus, the first mirror 20 of the second embodiment can be formed, so that the light source (micro heater 23) can be integrated with the first mirror 20.

According to the second embodiment, heating efficiency and light-emitting efficiency can be improved, because the micro heater 23 is arranged on the membrane bottom film 25.

Third Embodiment

If heat is radiated from the micro heater 23 through the membrane to the silicon substrate 110 or outside, the radiated heat may become a loss of heat. In contrast, in a third embodiment, the micro heater 23 has a bridge structure in order to reduce the heat radiation toward the silicon substrate 110. The other parts in the third embodiment may be made similar to the above embodiments.

Figure 8A:
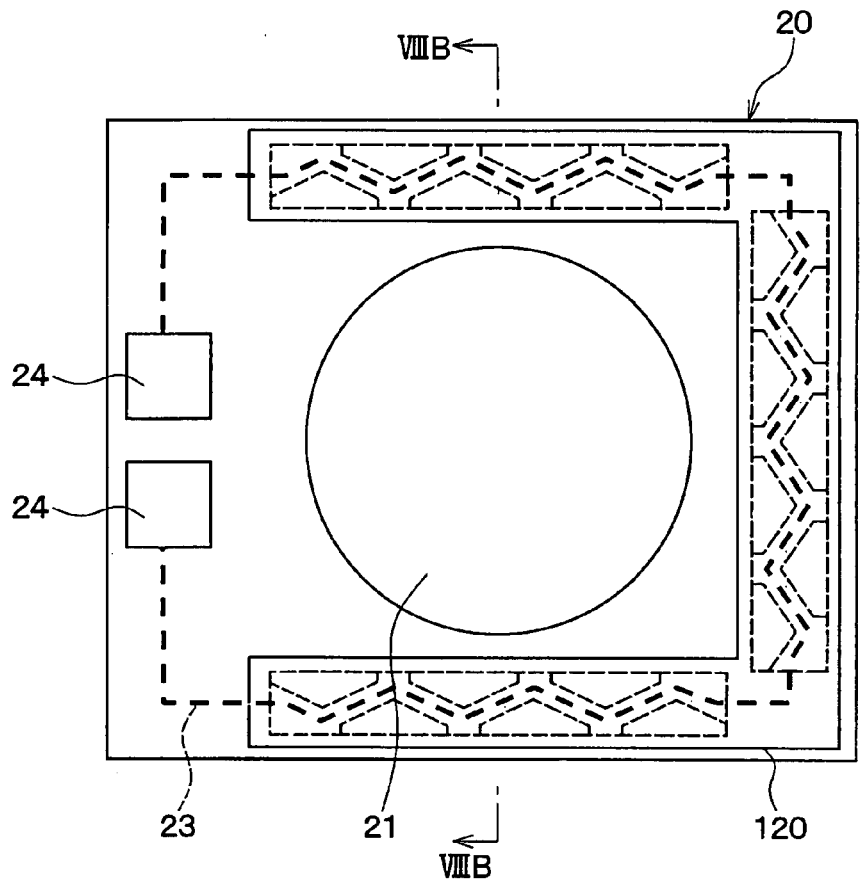
FIG. 8A is a schematic plan view showing a first mirror according to a third embodiment of the present invention.

As shown in FIG. 8A, a micro heater 23 (i.e., light source) and an electrode 24 are formed on a peripheral part of a front surface of a first mirror 20. The concave surface 21 is formed on the same front surface side. The micro heater 23 has a triangle wave shape, for example, above the silicon substrate 110.

Figure 8B:
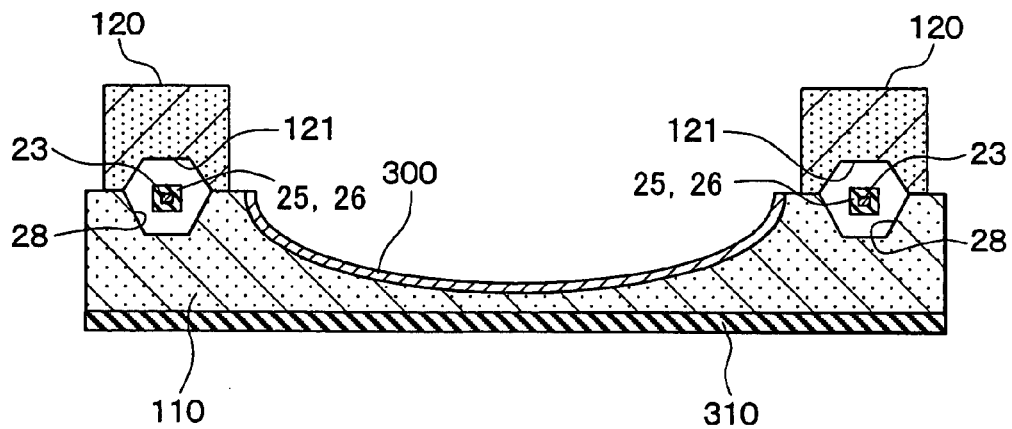
FIG. 8B is a schematic cross-sectional view taken along line VIIIB-VIIIB in FIG. 8A.

As shown in FIG. 8B, the micro heater 23 is disposed between the membrane bottom film 25 and the membrane top film 26, and has the bridge structure due to the membrane constructed with the membrane bottom film 25 and the membrane top film 26. That is, the micro heater 23 is disposed between a concave part 28 of the silicon substrate 110 and a concave part 121 of a vacuum sealing board 120. A space formed between the concave part 28 of the silicon substrate 110 and the concave part 121 of the vacuum sealing board 120 is in a vacuum.

Next, a method of producing the first mirror 20 of the third embodiment will be described with reference to FIGS. 9A, 9B, 9C and 9D. The third embodiment has the same processes shown in FIGS. 4A, 4B, 4C, 4D and 4E of the first embodiment and FIG. 7A of the second embodiment. In order to form the membrane, a substrate made of Si(100) is used as the silicon substrate 110.

Figure 9A:
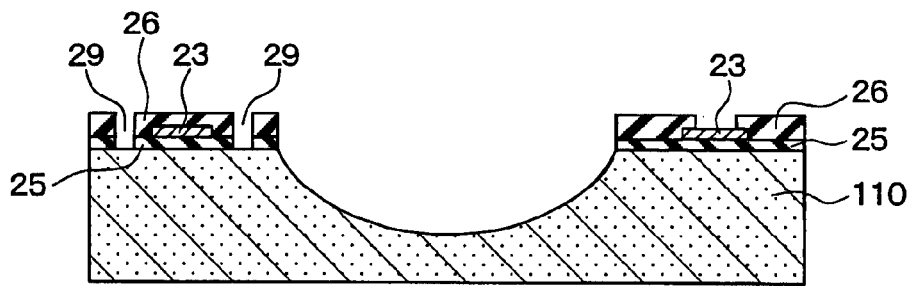
FIG. 9A is a schematic cross-sectional view showing a process of etching.

As shown in FIG. 9A, a part of the membrane top film 26 is removed by etching in order to arrange the electrode 24 for supplying electricity to the micro heater 23. Further, the membrane bottom film 25 and the membrane top film 26 formed on the concave surface 21 are removed by etching. Furthermore, in order to form the bridge structure of the micro heater 23, a part of the membrane bottom film 25 and the membrane top film 26 is removed by etching, so that an opening 29 can be formed at each (left and right) periphery side of the micro heater 23.

Figure 9B:
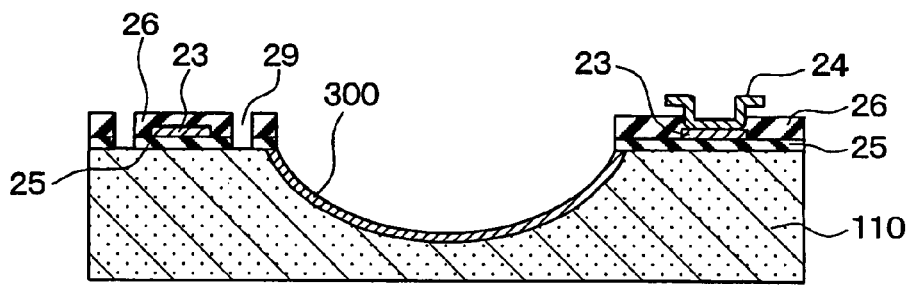
FIG. 9B is a schematic cross-sectional view showing a process of forming a reflection film and an electrode.

As shown in FIG. 9B, similarly to FIG. 7C, the reflection film 300 is formed on the concave surface 21, and the electrode 24 is arranged at the etched part of the membrane top film 26.

Figure 9C:
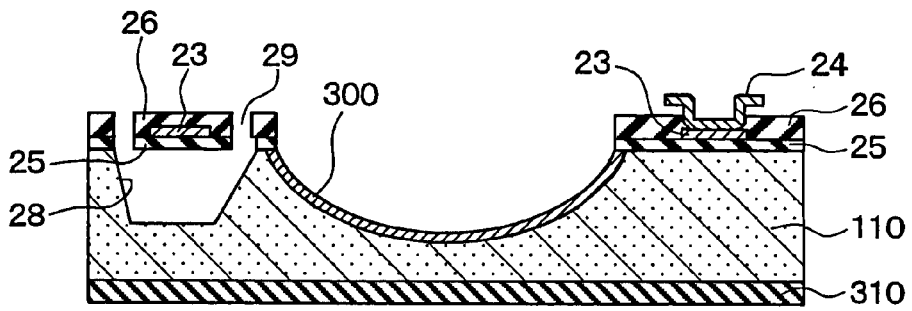
FIG. 9C is a schematic cross-sectional view showing a process of forming an antireflection film and a concave part and FIG. 9D is a schematic cross-sectional view showing a process of forming a vacuum sealing board.

As shown in FIG. 9C, a SiN film is formed on the back face of the silicon substrate 110 as the antireflection film 310, and the silicon substrate 110 is soaked in a silicon etching liquid from the front surface. Therefore, anisotropic etching is performed in the silicon substrate 110 from the opening 29. That is, the silicon substrate 110 opposing to the micro heater 23 is removed, so that the concave part 28 of the silicon substrate 110 can be formed. Thus, the bridge structure of the membrane constructed with the membrane bottom film 25 and the membrane top film 26 can be formed.

Figure 9D:
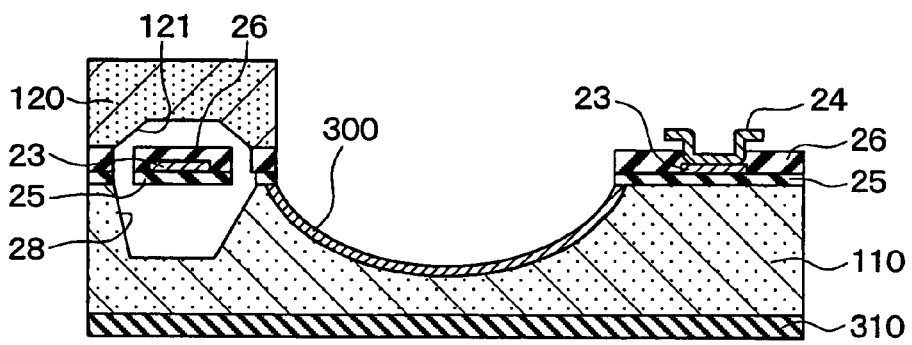

As shown in FIG. 9D, the vacuum sealing board 120 having the concave part 121 is connected to the silicon substrate 110 through the membrane such that the bridge structure is sealed in a vacuum.

Thus, the micro heater 23 is sealed in the vacuum between the silicon substrate 110 and the vacuum sealing board 120. Therefore, heat radiation from the micro heater 23 to air can be prevented, so that the micro heater 23 can have high efficiency.

Fourth Embodiment

Figure 10A:
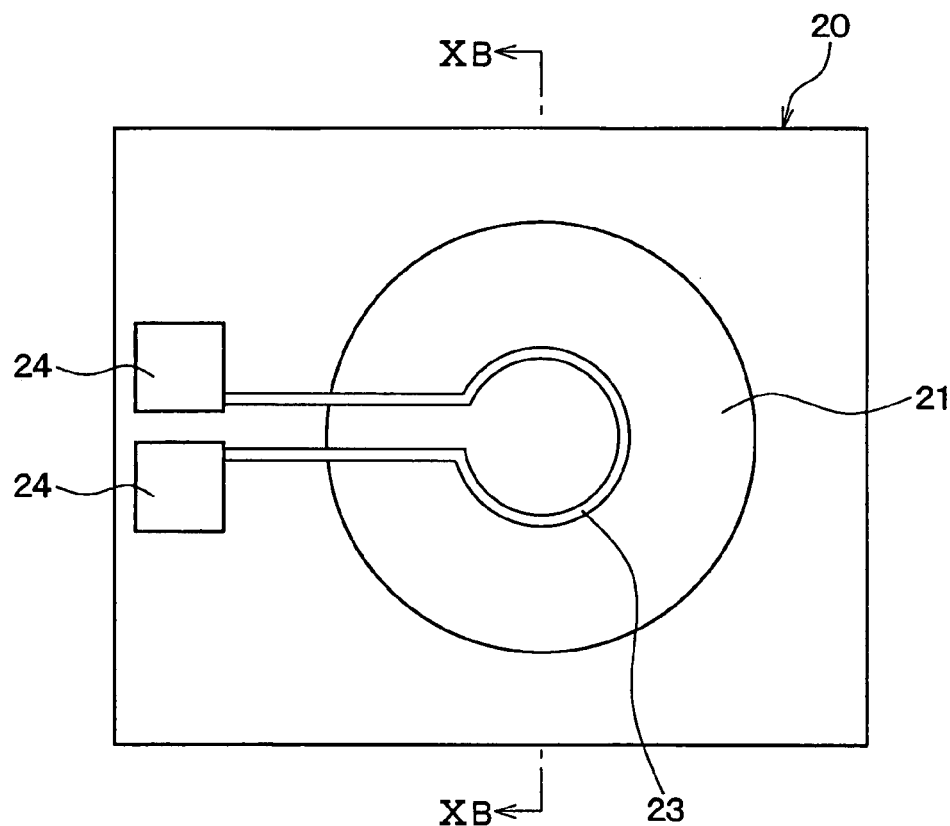
FIG. 10A is a schematic plan view showing a first mirror according to a fourth embodiment of the present invention.
Figure 10B:
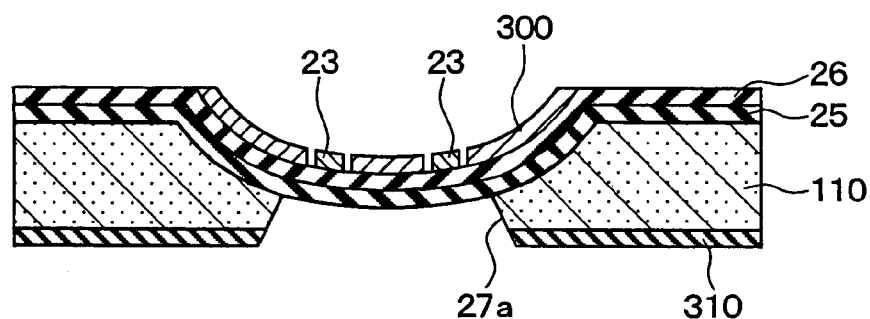
FIG. 10B is a schematic cross-sectional view taken along line XB-XB in FIG. 10A.

The micro heater 23 is arranged on the peripheral part of the first mirror 20 in the second and third embodiments. In a fourth-embodiment, as shown in FIGS. 10A and 10B, a micro heater 23 is arranged on a concave surface 21, so that efficiency of the multiple reflections of light between the mirrors 20, 30 can be more increased. The other parts in the fourth embodiment may be made similar to the above embodiments.

As shown in FIG. 10A, the micro heater 23 (i.e., light source) is formed on the concave surface 21 of the first mirror 20, and a wiring extending from the micro heater 23 is connected to the electrode 24 disposed on the peripheral part of the first mirror 20. Further, as shown in FIG. 10B, a concave part 27a is provided in a back face of the first mirror 20, and the micro heater 23 is embedded in the reflection film 300 constructing a membrane together with the membrane bottom film 25 and the membrane top film 26.

Next, a method of producing the first mirror 20 of the fourth embodiment will be described with reference to FIGS. 11A, 11B and 11C. The fourth embodiment has the same processes shown in FIGS. 4A, 4B, 4C, 4D and 4E of the first embodiment. In order to form the membrane, a substrate made of Si(100) is used as the silicon substrate 110.

Figure 11A:
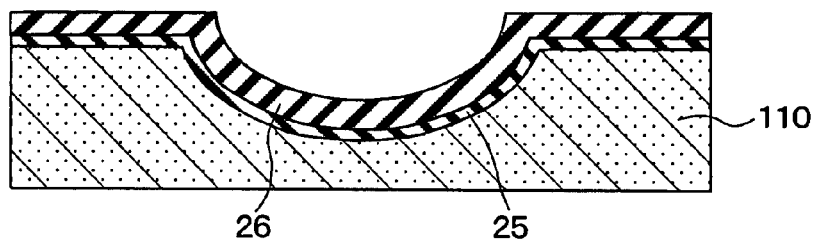
FIG. 11A is a schematic cross-sectional view showing a process of forming a membrane.

As shown in FIG. 11A, the membrane constructed with the membrane bottom film 25 and the membrane top film 26 is formed on the front surface of the silicon substrate 110. Similarly to FIG. 7A, the low-pressure chemical vapor deposition (LPCVD) method is used to form an insulation film combining a SiN film and a $SiO_2$ film as the membrane bottom film 25. Then, another insulation film combining the SiN film and the $SiO_2$ film is formed on the membrane bottom film 25, as the membrane top film 26.

Figure 11B:
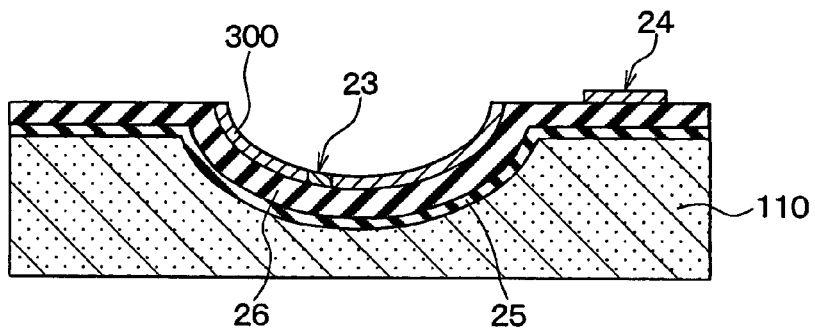
FIG. 11B is a schematic cross-sectional view showing a process of forming a reflection film, a micro heater and an electrode.

As shown in FIG. 11B, gold (Au) is evaporated and deposited on the membrane top film 26 to form the reflection film 300 having a thickness of about 0.2 μm and a reflection characteristic in a wide band range. Then, a patterning of the reflection film 300 is performed. Further, a patterning of the micro heater 23 shown in FIG. 10A is performed.

Figure 11C:
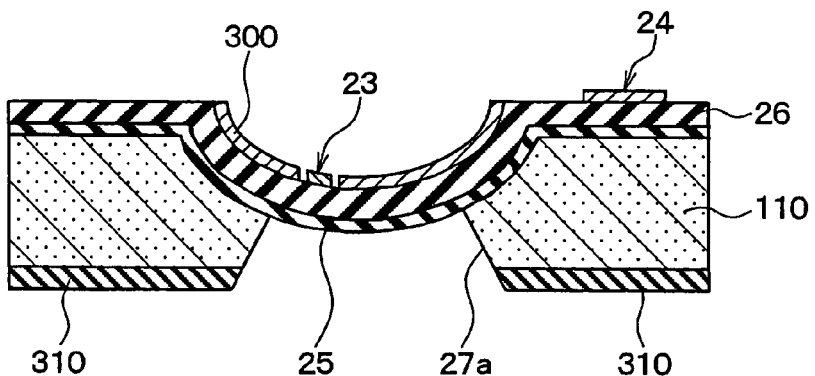
FIG. 11C is a schematic cross-sectional view showing a process of forming an antireflection film and etching.

As shown in FIG. 11C, a SiN film is formed on a back face of the silicon substrate 110 as the antireflection film 310. Further, the antireflection film 310 opposing to the micro heater 23 is removed, and the silicon substrate 110 is soaked in the silicon etching liquid from the back face, so that anisotropic etching is performed at the back face of the silicon substrate 110. Thereby, a concave part 27a can be formed, so that the concave surface 21 having the micro heater 23 can be made into the membrane. Thus, the micro heater 23 can be formed on the concave surface 21 of the first mirror 20.

Fifth Embodiment

The concave surface 21, 31 of the mirror 20, 30 is formed by using the mask 200 shown in FIG. 3A in the above embodiments. In this case, as shown in FIG. 3B, a part of the silicon substrate 110 is remained as a tube-shaped wall due to the mask 200, and the wall may be broken by a distortion of the silicon substrate 110 or washing.

Figure 12:
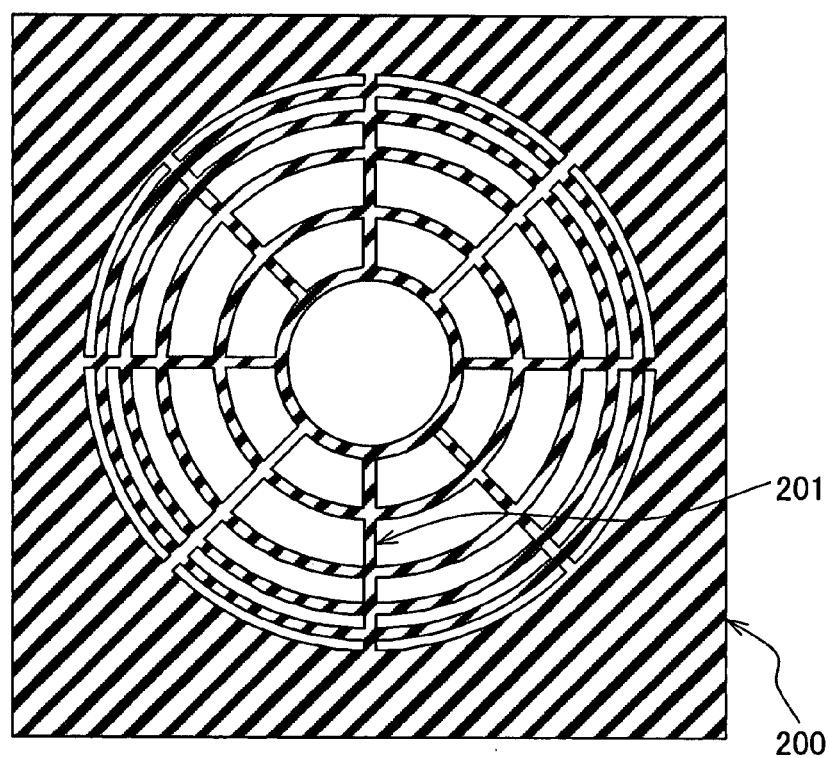
FIG. 12 is a plan view showing a mask according to a fifth embodiment of the present invention.

In a fifth embodiment, as shown in FIG. 12, the plural concentric circles of the mask 200 are connected by a beam 201, in order to secure a strength of the silicon substrate 110, when the etching is performed to form the concave surface 21, 31 of the mirror 20, 30. The other parts in the fifth embodiment may be made similar to the above embodiments.

The beam 201 has a linear shape passing through a center of the concentric circles. Plural beams 201 are provided in FIG. 12. However, only one beam 201 may be provided. The beam 201 is approximately perpendicular to a tangent line of the concentric circle.

The beam 201 has a width approximately similar to that of the concentric circle constructing the mask 200, as shown in FIG. 12. However, the width of the beam 201 may be different from that of the concentric circles.

According to the fifth embodiment, when the concentric circles constructing the mask 200 are connected by the beam 201, the strength of the silicon substrate 110 can be secured. Thus, a crack of the silicon substrate 110 can be reduced.

Other Embodiments

In the above embodiments, the thermally oxidizing process is performed in FIG. 4C, and the etching is performed in FIG. 4D. Alternatively, after the process shown in FIG. 4B, a silicon wet etching process may be performed. Further, the processes shown in FIGS. 4C and 4D may be repeated. Thus, the projections and recessions on the front surface of the silicon substrate 110 can be more reduced.

In the above embodiments, the reflection film 300 is made of gold. Alternatively, the reflection film 300 may be a multilayer film made of Ge or ZnSe.

In the above embodiments, the mirror 20, 30 is made of the silicon substrate 110. Alternatively, the mirror 20, 30 may be a wafer made of a material such as Ge capable of forming an oxide film thereon.

Figure 13A:
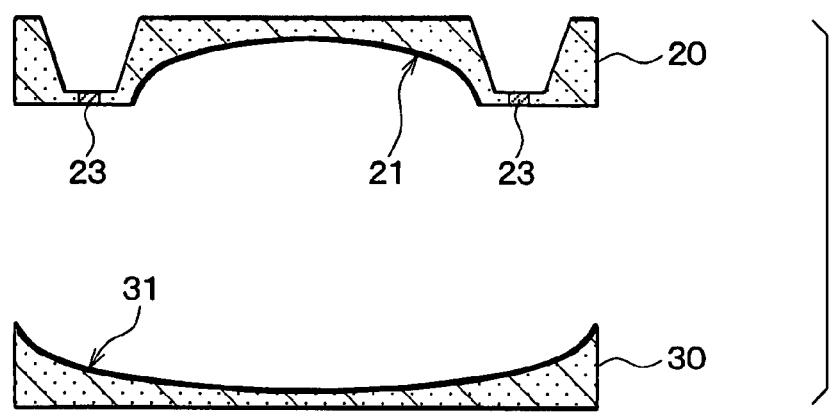
FIG. 13A is a schematic cross-sectional view showing a first mirror and a second mirror according to another embodiment, in which a diameter of the second mirror is larger than that of the first mirror.

In the above embodiments, the concave surface 21 of the first mirror 20 and the concave surface 31 of the second mirror 30 have approximately the same diameter. As shown in FIG. 13A, the concave surface 31 of the second mirror 30 may have a diameter larger than that of the concave surface 21 of the first mirror 20. In this case, light emitted from the micro heater 23 can be efficiently and multiply reflected.

Figure 13B:
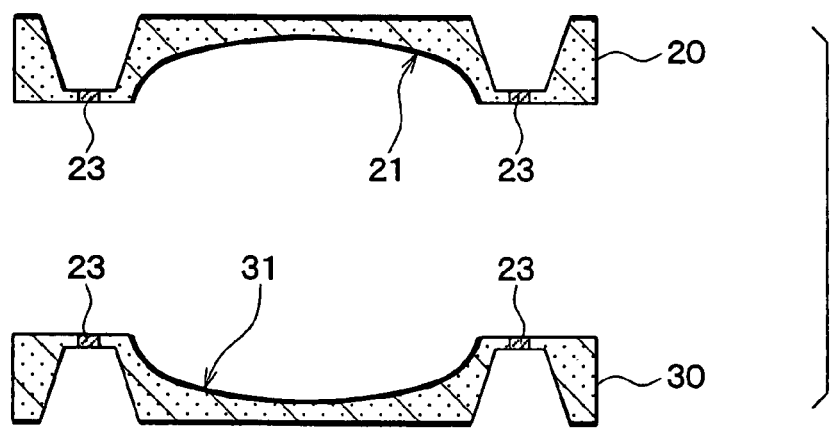
FIG. 13B is a schematic cross-sectional view showing a first mirror and a second mirror according to another embodiment, in which the first and second mirrors have micro heaters, respectively.

In the above embodiments, the micro heater 23 is formed in the first mirror 20. As shown in FIG. 13B, the micro heater 23 may be formed in each of the first mirror 20 and the second mirror 30. In this case, an amount of light can be twice compared with that in the above embodiments.

In the third embodiment, the micro heater 23 has the bridge structure, and the micro heater 23 is sealed in a vacuum. Alternatively, when the micro heater 23 has the bridge structure, the micro heater 23 may not be sealed in a vacuum. Alternatively, when the micro heater 23 is sealed in the vacuum, the micro heater 23 may not have the bridge structure. In these cases, sufficient amount of light can be provided.

The substrate 110 is capable of being oxidized, and includes a separating part for separating the openings of the mask 200. The separating part of the substrate 110 is removed by oxidizing, in order to form the concave surface 21, 31. Thus, a surface treatment can be easily performed after the surface of the substrate 110 is processed by the etching. Especially when a width of the separating part is narrow, the separating part can be easily removed.

The substrate 110 includes the separating part for separating the openings of the mask 200, and the separating part of the substrate 110 may be removed by a wet-etching in order to form the concave surface 21, 31. In this case, the etching of the substrate 110 can be easily performed by soaking the substrate 110 into an etching liquid.

The substrate 110 is smoothed by a thermal treatment in a hydrogen atmosphere, after the separating part of the substrate 110 is removed. Further, the surface of the substrate 110 may be removed by oxidizing, after the substrate 110 is smoothed. The removing of the surface of the substrate 110 and the smoothing of the substrate 100 may be repeated a plurality of times, after the substrate 110 is smoothed. In this case, projections and recessions on the substrate 110 generated in the processing of the substrate 110 can be more reduced.

The reflection film 300 may be formed by applying a metal film such as a gold having a wide reflection characteristic relative to infrared light. Further, the metal film may be patterned. The patterned metal film may be used as a light source, for example.

Such changes and modifications are to be understood as being within the scope of the present invention as defined by the appended claims.

What is claimed is:

1. A method of producing a structure by three-dimensionally processing a flat member, the method comprising:
    preparing a substrate as the flat member;
    forming an etching mask on the substrate, wherein the etching mask has at least two openings and areas of the two openings are different from each other; and forming at least a part of a three-dimension surface shape of the structure on a surface of the substrate by a dry-etching on the substrate in accordance with the area of the opening of the etching mask, wherein the substrate includes a separating part for separating the openings, the separating part of the substrate is removed by an isotropic wet-etching in the forming of at least the part of the three-dimension surface shape of the structure, and the substrate is smoothed by a thermal treatment in a hydrogen atmosphere, after the separating part of the substrate is removed.

2. A method of producing a structure by three-dimensionally processing a flat member, the method comprising:

preparing a substrate as the flat member;

forming an etching mask on the substrate, wherein the etching mask has at least two openings and areas of the two openings are different from each other; and forming at least a part of a three-dimension surface shape of the structure on a surface of the substrate by a dry-etching on the substrate in accordance with the area of the opening of the etching mask, wherein the substrate is capable of being oxidized, and includes a separating part for separating the openings, the separating part of the substrate is oxidized and the oxidized separating part is removed in the forming of at least the part of the three-dimension surface shape of the structure, and the substrate is smoothed by a thermal treatment in a hydrogen atmosphere, after the oxidized separating part is removed.

3. The method according to claim 1, wherein the removing of the separating part of the substrate and the smoothing of the substrate are repeated a plurality of times, after the substrate is smoothed.

4. A method of producing a structure by three-dimensionally processing a flat member, the method comprising:

preparing a substrate as the flat member;

forming an etching mask on the substrate, wherein the etching mask has at least two openings and areas of the two openings are different from each other; and forming at least a part of a three-dimension surface shape of the structure on a surface of the substrate by a dry-etching on the substrate in accordance with the area of the opening of the etching mask, wherein the opening is one of a plurality of openings, the plurality of openings has an area, which gradually becomes larger from a peripheral part of the etching mask to a center part of the etching mask such that a concave surface is formed on the substrate as the three-dimension surface shape of the structure, the etching mask has a shape of a plurality of concentric circles having different diameters, the opening is provided between two adjacent concentric circles, and the plurality of openings has an area, which gradually becomes smaller toward an outside diameter direction of the concentric circle, and further comprising:

forming a reflection film on the concave surface, after the concave surface is formed on the substrate by the dry-etching and removing a separating part for separating the openings, and forming an antireflection film on an approximately flat face of the substrate, which is opposite to the concave surface.

5. The method according to claim 4, wherein
the reflection film is formed by applying a metal film.

6. A method of producing a structure by three-dimensionally processing a flat member, the method comprising:

preparing a substrate as the flat member;

forming an etching mask on the substrate, wherein the etching mask has at least two openings and areas of the two openings are different from each other; and forming at least a part of a three-dimension surface shape of the structure on a surface of the substrate by a dry-etching on the substrate in accordance with the area of the opening of the etching mask, wherein the opening is one of a plurality of openings, the plurality of openings has an area, which gradually becomes larger from a peripheral part of the etching mask to a center part of the etching mask such that a concave surface is formed on the substrate as the three-dimension surface shape of the structure, the etching mask has a shape of a plurality of concentric circles having different diameters, the opening is provided between two adjacent concentric circles, and the plurality of openings has an area, which gradually becomes smaller toward an outside diameter direction of the concentric circle, and further comprising:

forming an insulation film on the substrate outside of the concave surface, after the concave surface is formed on the substrate by the dry-etching and removing a separating part for separating the openings; and forming a micro heater by patterning a metal film on the insulation film.

7. A method of producing a structure by three-dimensionally processing a flat member, the method comprising:

preparing a substrate as the flat member;

forming an etching mask on the substrate, wherein the etching mask has at least two openings and areas of the two openings are different from each other; and forming at least a part of a three-dimension surface shape of the structure on a surface of the substrate by a dry-etching on the substrate in accordance with the area of the opening of the etching mask, wherein the opening is one of a plurality of openings, the plurality of openings has an area, which gradually becomes larger from a peripheral part of the etching mask to a center part of the etching mask such that a concave surface is formed on the substrate as the three-dimension surface shape of the structure, the etching mask has a shape of a plurality of concentric circles having different diameters, the opening is provided between two adjacent concentric circles, the plurality of openings has an area, which gradually becomes smaller toward an outside diameter direction of the concentric circle, and the etching mask includes a beam connecting the concentric circles.

8. The method according to claim 7, wherein
the beam is approximately perpendicular to a tangent line of the concentric circle.

9. The method according to claim 7, wherein
the beam has a width approximately equal to that of the concentric circle.

* * * * *